US009833526B2

(12) United States Patent
Agafonov et al.

(10) Patent No.: US 9,833,526 B2
(45) Date of Patent: Dec. 5, 2017

(54) ULTRAVIOLET ILLUMINATOR

(71) Applicant: Sensor Electronic Technology, Inc., Columbia, SC (US)

(72) Inventors: Igor Agafonov, Columbia, SC (US); Alexander Dobrinsky, Loudonville, NY (US); Michael Shur, Latham, NY (US); Remigijus Gaska, Columbia, SC (US); Saulius Smetona, Concord, NC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 14/630,692

(22) Filed: Feb. 25, 2015

(65) Prior Publication Data
US 2015/0238645 A1 Aug. 27, 2015

Related U.S. Application Data

(60) Provisional application No. 61/944,359, filed on Feb. 25, 2014.

(51) Int. Cl.
*A61L 2/10* (2006.01)
*A23L 3/28* (2006.01)

(52) U.S. Cl.
CPC .. *A61L 2/10* (2013.01); *A23L 3/28* (2013.01)

(58) Field of Classification Search
CPC ..................................... A61L 2/10; A61L 2/24
See application file for complete search history.

(56) References Cited

U.S. PATENT DOCUMENTS

| 7,553,456 | B2 | 6/2009 | Gaska et al. | |
| D631,617 | S * | 1/2011 | Morton | D30/160 |
| 8,277,734 | B2 | 10/2012 | Koudymov et al. | |
| 8,384,047 | B2 | 2/2013 | Shur et al. | |
| 2009/0100853 | A1* | 4/2009 | Bryant | F25D 31/003 62/264 |
| 2009/0117001 | A1* | 5/2009 | Hyde | E05B 1/0069 422/24 |
| 2010/0007492 | A1* | 1/2010 | Ressler | A61L 2/10 340/540 |
| 2010/0296971 | A1 | 11/2010 | Gaska et al. | |
| 2012/0008313 | A1* | 1/2012 | Plumb | A47G 33/06 362/184 |
| 2012/0135156 | A1* | 5/2012 | Cakmak | B29C 41/28 427/508 |

(Continued)

*Primary Examiner* — Sean Luck
(74) *Attorney, Agent, or Firm* — LaBatt, LLC

(57) ABSTRACT

A solution for disinfecting an area using ultraviolet radiation is provided. The solution can include an enclosure including at least one ultraviolet transparent window and a set of ultraviolet radiation sources located adjacent to the at least one ultraviolet transparent window. The set of ultraviolet radiation sources can be configured to generate ultraviolet radiation directed through the at least one ultraviolet transparent window. An input unit can be located on the enclosure and configured to generate an electrical signal in response to pressure applied to the enclosure. A control unit can be configured to manage the ultraviolet radiation by monitoring the electrical signal generated by the input unit and controlling, based on the monitoring, the ultraviolet radiation generated by the set of ultraviolet radiation sources.

20 Claims, 6 Drawing Sheets

(56) References Cited

U.S. PATENT DOCUMENTS

| | | | |
|---|---|---|---|
| 2012/0321509 A1* | 12/2012 | Bak | A61L 2/10 422/24 |
| 2013/0048545 A1 | 2/2013 | Shatalov et al. | |
| 2013/0270445 A1 | 10/2013 | Gaska et al. | |
| 2014/0008675 A1 | 1/2014 | Shatalov et al. | |
| 2014/0060094 A1 | 3/2014 | Shur et al. | |
| 2014/0060095 A1 | 3/2014 | Shur et al. | |
| 2014/0060096 A1 | 3/2014 | Shur et al. | |
| 2014/0060104 A1 | 3/2014 | Shur et al. | |
| 2014/0061509 A1 | 3/2014 | Shur et al. | |
| 2014/0183377 A1 | 7/2014 | Bettles et al. | |
| 2014/0202962 A1 | 7/2014 | Bilenko et al. | |
| 2014/0264070 A1 | 9/2014 | Bettles et al. | |
| 2014/0264076 A1 | 9/2014 | Bettles et al. | |

* cited by examiner

ULTRAVIOLET ILLUMINATOR

REFERENCE TO RELATED APPLICATIONS

The current application claims the benefit of U.S. Provisional Application No. 61/944,359, titled "Ultraviolet Autonomous Illuminator," which was filed on 25 Feb. 2014, and which is hereby incorporated by reference.

TECHNICAL FIELD

The disclosure relates generally to ultraviolet illumination, and more particularly, to a solution for preserving, disinfecting, and/or the like, stored items within an area using ultraviolet radiation.

BACKGROUND ART

Reliable, hygienic storage of sanitary and biological items, such as food, is a major problem. For example, the problem is present throughout the food industry, e.g., manufacturers, retailers, restaurants, and in every household, and is especially significant for food service establishments, in which related issues of food quality control also are significant. In addition to food storage and quality control in fixed locations (e.g., a refrigerator) where access to electricity is readily available, proper food storage and quality control also is important in situations for which access to unlimited electricity and/or a stationary storage device, such as a refrigerator, is not available, such as picnics, camping, mobile food kiosks, hospitality or battlefield meal locations, search and rescue, etc. In addition to food, other stored items also require hygienic storage. For example, medical and chemical equipment, construction wood, etc., also require storage in a biologically safe environment. Since ambient temperature significantly affects bacterial activity, effective control of the ambient temperature is an important tool in ensuring reliable, hygienic storage of various items.

Fresh food products can be processed using ultraviolet light as a germicidal medium to reduce the food-born microbial load. Water has been treated with ultraviolet light to provide safe drinking water for quite some time. Fruit and vegetable products capable of being pumped through a system generally are very suitable for processing by ultraviolet light to reduce the microbial load. Today, most of these products are pasteurized to obtain microbiologically safe and nutritious products. However, pasteurization can change the taste and flavor of such products because of the temperature and processing time. Juices from different sources can be treated by exposure to ultraviolet light at different doses. On the other hand, variables such as exposure time, type of fruit product, juice color and juice composition, among other variables, need to be studied to obtain fruit products with reduced microbial load, increased shelf life and adequate sensory and nutritional characteristics. Reduction of microbial load through ultraviolet light application as a disinfection medium for food products other than liquids also is being studied. Moreover, ultraviolet technology could be a source for pasteurization of liquids, or disinfection of solid foods as an alternative technology, instead of thermal treatment or application of antimicrobial compounds.

In general, ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

Various approaches have sought to use ultraviolet light to disinfect a compartment, such as compartments found in refrigerators. For example, one approach proposes a plurality of small, low current UV lights which utilize the standard circuitry of the refrigerator to power the UV light source. Another approach uses a UV lamp installed in a top portion of the refrigerator and reflective lining throughout the interior to reflect the UV radiation throughout the compartment. Another approach provides a UV system with a single UV source attached to an internal sidewall of a refrigerator to radiate light to the entire compartment, or in the alternative, provide UV exposure to a limited compartment. Still another approach proposes an air cleaner for an internal compartment of a refrigerator, which utilizes a UV filter to reduce pathogens in the re-circulated air. Still another approach provides a refrigerator with UV light irradiation components to eradicate low-level light from the storage containers contained therein to promote freshness of foodstuffs.

SUMMARY OF THE INVENTION

Aspects of the invention provide a solution for preserving, disinfecting, and/or the like, stored items within an area using ultraviolet radiation. An embodiment provides an enclosure including at least one ultraviolet transparent window and a set of ultraviolet radiation sources located adjacent to the at least one ultraviolet transparent window. The set of ultraviolet radiation sources can be configured to generate ultraviolet radiation that is directed through the at least one ultraviolet transparent window. An input unit can be located on the enclosure and configured to generate an electrical signal in response to pressure applied to the enclosure. A control unit can be configured to manage the ultraviolet radiation by monitoring the electrical signal generated by the input unit and controlling, based on the monitoring, the ultraviolet radiation generated by the set of ultraviolet radiation sources.

A first aspect of the invention provides a system comprising: an enclosure including at least one ultraviolet transparent window; a set of ultraviolet radiation sources located adjacent to the at least one ultraviolet transparent window, the set of ultraviolet radiation sources configured to generate ultraviolet radiation directed through the at least one ultraviolet transparent window; an input unit located on the enclosure and configured to generate an electrical signal corresponding to pressure applied to at least one portion of the enclosure; and a control unit configured to manage the ultraviolet radiation by performing a method comprising: monitoring the electrical signal generated by the input unit;

and controlling, based on the monitoring, the ultraviolet radiation generated by the set of ultraviolet radiation sources.

A second aspect of the invention provides an enclosure, comprising: at least one ultraviolet transparent region located on a surface of the enclosure; a set of ultraviolet radiation sources located within the enclosure, the set of ultraviolet radiation sources configured to generate ultraviolet radiation directed through the at least one ultraviolet transparent region; an input unit located on the enclosure and configured to generate an electrical signal corresponding to pressure applied to at least one region of the enclosure; and a control unit configured to manage the ultraviolet radiation by performing a method comprising: monitoring the electrical signal generated by the input unit; and controlling, based on the monitoring, the ultraviolet radiation generated by the set of ultraviolet radiation sources.

A third aspect of the invention provides a system comprising: an area including a fluid for disinfection; and at least one enclosure submerged within the fluid, the at least one enclosure, comprising: at least one ultraviolet transparent window; a set of ultraviolet radiation sources located within the enclosure, the set of ultraviolet radiation sources configured to generate ultraviolet radiation directed through the at least one ultraviolet transparent window; an input unit located on the enclosure and configured to generate an electrical signal corresponding to pressure applied to at least one region of the enclosure; and a control unit configured to manage the ultraviolet radiation by performing a method comprising: monitoring the electrical signal generated by the input unit; and controlling, based on the monitoring, the ultraviolet radiation generated by the set of ultraviolet radiation sources.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for preserving, disinfecting, and/or the like, stored items within an area using ultraviolet radiation. An embodiment provides an enclosure including at least one ultraviolet transparent window. A set of ultraviolet radiation sources can be located adjacent to the at least one ultraviolet transparent window and configured to generate ultraviolet radiation directed through the at least one ultraviolet transparent window. An input unit can be located on the enclosure and configured to generate an electrical signal in response to pressure applied to the input unit. A control unit can be configured to manage the ultraviolet radiation by monitoring the electrical signal generated by the input unit and controlling, based on the monitoring, the ultraviolet radiation generated by the set of ultraviolet radiation sources. At least one enclosure can be used to autonomously preserve and disinfect items within an area using the ultraviolet radiation.

As used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through. In an embodiment, the ultraviolet transparent structure is formed of a material and has a thickness, which allows at least ten percent of the ultraviolet radiation to pass there through at a normal incidence to an interface of the material/structure. As used herein, unless otherwise noted, the term "set" means one or more (i.e., at least one) and the phrase "any solution" means any now known or later developed solution.

Figure 1:
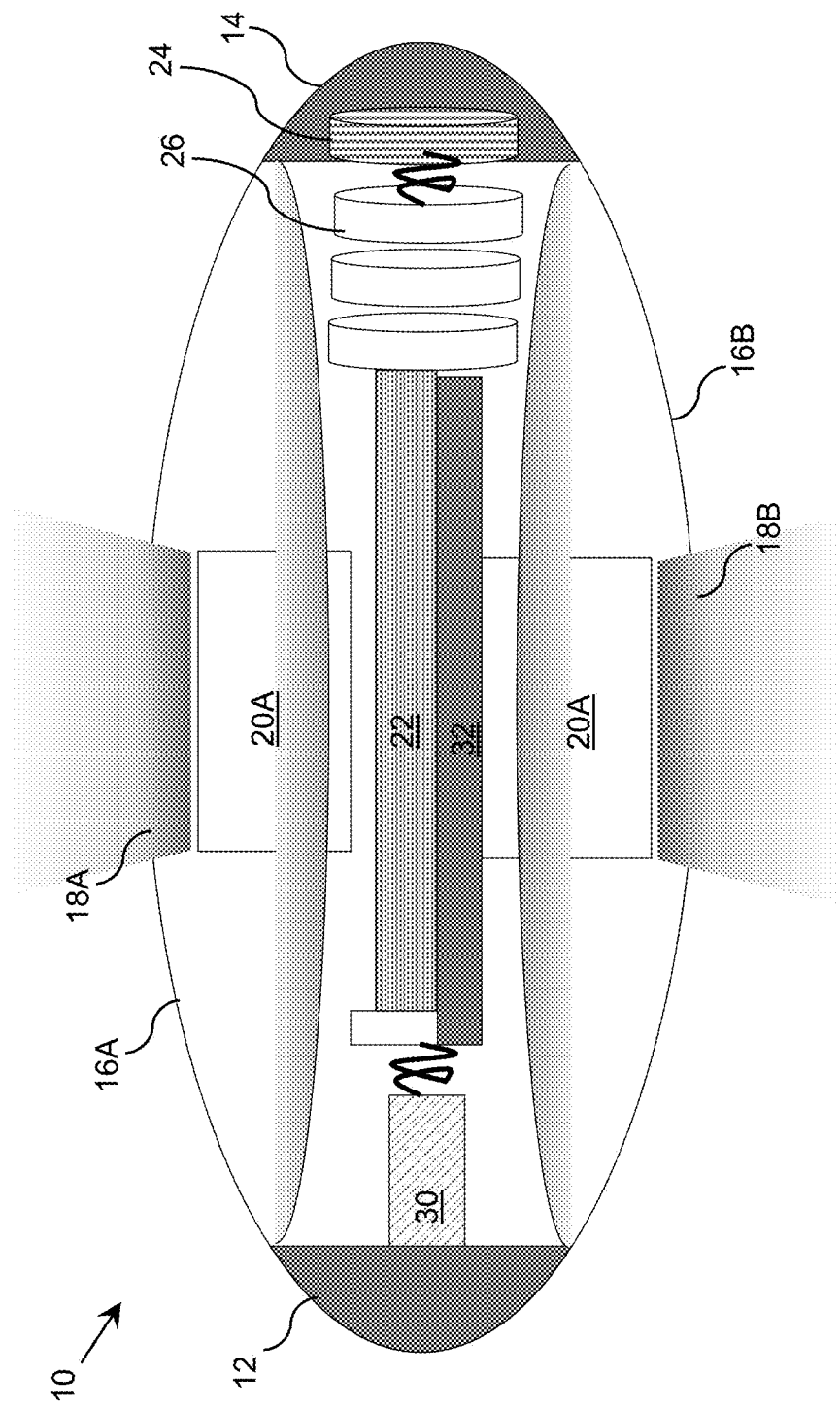
FIG. 1 shows an illustrative enclosure according to an embodiment.

Turning to the drawings, FIG. 1 shows an enclosure 10 according to an embodiment. The enclosure 10 is shown as a prolate spheroid shape (e.g., football) with a first end 12 and a second end 14. The first end 12 and the second end 14 are connected by elongated sides 16A, 16B. However, it is understood that the prolate spheroid shape is only illustrative and that the enclosure 10 can be any shape. In an embodiment, the enclosure 10 can have at most a volume of approximately 75 cm$^3$.

Figure 2:
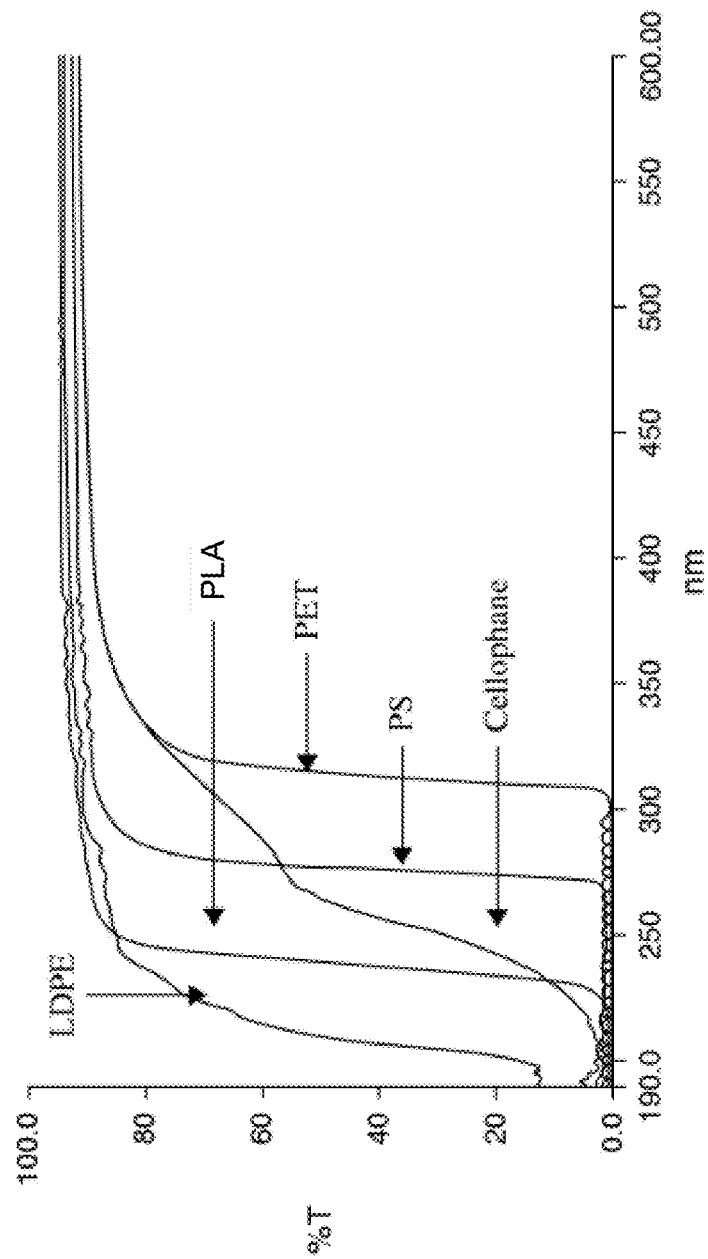
FIG. 2 shows transmission properties for various transparent polymers.

The enclosure 10 includes at least one ultraviolet transparent window 18A, 18B located on the elongated sides 16A, 16B. Although two ultraviolet radiation transparent windows are shown for the enclosure 10, it is understood that the enclosure 10 can include any number of one or more ultraviolet transparent windows. The at least one ultraviolet transparent window 18A, 18B can be formed of any ultraviolet transparent material, such as sapphire, quartz, an ultraviolet transparent polymer, and/or the like. In an embodiment, the at least one ultraviolet transparent window 18A, 18B can include at least one ultraviolet transparent polymer, such as, for example, fluorinated ethylene propylene (FEP), fluorinated ethylene propylene co-polymer (EFEP), polyactic acid (PLA), low-density polyethylene (LDPE), polystyrene (PS), polyethylene terephthalate (PET), cellophane, and/or the like. FIG. 2 shows the transmission properties for these polymers. In particular, these polymers, such as PLA and LDPE, are sufficiently transparent to transmit ultraviolet radiation of certain wavelengths. These polymers also provide proper protection for the ultraviolet radiation sources from the environment.

Turning back to FIG. 1, the enclosure 10 can include a set of ultraviolet radiation sources 20A, 20B located adjacent to the at least one ultraviolet transparent window 18A, 18B. The set of ultraviolet radiation sources 20A, 20B can comprise any combination of one or more ultraviolet radiation emitters. For example, the set of ultraviolet radiation sources 20A, 20B can include a high intensity ultraviolet lamp (e.g., a high intensity mercury lamp), a discharge lamp, an ultraviolet light emitting diode (LED), super luminescent LEDs, laser diodes, and/or the like. In an embodiment, the set of ultraviolet radiation sources 20A, 20B includes a set of light emitting diodes manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). Additionally, the set of ultraviolet radiation sources 20A, 20B can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, through the ultraviolet transparent window 18A, 18B. Illustrative wave guiding structures include, but are not limited to, a plurality of ultraviolet fibers, each of which terminates at an opening, a diffuser, and/or the like.

The enclosure 10 can also include a control unit 22 configured to manage the set of ultraviolet radiation sources 20A, 20B by controlling the ultraviolet radiation generated by the set of ultraviolet radiation sources 20A, 20B. The control unit 22 can control one or more of: the intensity, wavelength, duration, time, and/or the like, of the ultraviolet radiation generated by the set of ultraviolet radiation sources 20A, 20B.

The control unit 22 can be configured to receive an electrical signal from sensors located adjacent to the first end 12 and the second end 14 of the enclosure 10. That is, each end 12, 14 can include a sensor configured to convert physical pressure applied to the corresponding end 12, 14 into a signal as an input for the control unit 22. In response, the control unit 22 can, for example, turn on or off the set of ultraviolet radiation sources 20A, 20B. More particularly, a pattern of the physical pressure applied to each end 12, 14 can provide a signal to the control unit 22 for a particular intensity, wavelength, duration, time, pattern, and/or the like, for the ultraviolet radiation generated by the set of ultraviolet radiation sources 20A, 20B. For example, the physical pressure applied to each end 12, 14 simultaneously can be a series of applied pressures of a minimum amount with a pause between each applied pressure, where the applied pressures and/or the pauses have a corresponding target time duration. In another embodiment, the physical pressure applied to each end 12, 14 can be a series of applied pressures with longer durations alternating with a series of applied pressures with shorter durations. In an embodiment, pressure is applied to each end 12, 14 substantially simultaneously. Alternatively, pressure can be applied to only to one end 12, 14 at a time. In another embodiment, the particular pattern of the applied pressure to the ends 12, 14 can also transmit more complicated information to the control unit 22. For example, the pressure applied to the ends 12, 14 can constitute a series of short and long pulses. It is understood that although the above examples describe an applied pressure to the ends 12, 14, physical pressure is not required to provide a signal to the control unit 22 and other solutions can be utilized. For example, in another embodiment, a capacitive touch to each end 12, 14 (e.g., without significant applied pressure) can provide a signal to the control unit 22 to turn on the set of ultraviolet radiation sources 20A, 20B.

In applying pressure to the first end 12 and/or the second end 14, it is understood that the ends 12, 14 can provide a waterproof seal to the interior of the enclosure 10. As seen in FIG. 1, the second end 14 can include a threading 24 for removing the second end 14. The threading 24 can provide a watertight seal between the second end 14 and the remaining portion of the enclosure 10. Although FIG. 1 shows threading for removably securing the second end 14 and the enclosure 10, it is understood that any form of connection that forms a watertight seal, such as a gasket, and/or the like, can be utilized to secure the second end 14 to the remaining portion of the enclosure 10. Furthermore, although threading is not shown between the enclosure 10 and the first end 12, it is understood that a similar connection can be provided.

The removal of the second end 14 (and/or the first end 12) allows for insertion and removal of one or more components located in the enclosure 10. For example, the second end 14 can be removed to replace a set of batteries 26 used for powering the set of ultraviolet radiation sources 20A, 20B, the control unit 22, and any other components within the enclosure 10. Although a battery 26 is shown in FIG. 1, it is understood that the enclosure 10 can include other forms for a power component. For example, the enclosure 10 can include a vibration power generator based on magnetic oscillations or stresses developed on a piezoelectric crystal. In an embodiment, a component 30 within the enclosure 10 can be a vibrational power generator. The component 30 can be connected to a piezoelectric crystal 32 via an elastic spring. In another embodiment, the power component can comprise a super capacitor that is rechargeable. In still another embodiment, the battery 26 can be rechargeable and recharged by, for example, the vibration power generator, a wireless charging system from an electromagnetic signal, and/or the like. For a typical LED, operating at 20 mA, with a coin battery rated 225 mAH, the LED can operate in a continuous mode for about 10 hours. A typical disinfection session may last on the order of 10 minutes, thus resulting in approximately 60 disinfection sessions from a single enclosure before the battery would need to be recharged or changed. For extended life, two or more coin batteries can be employed within the enclosure 10.

Figure 3:
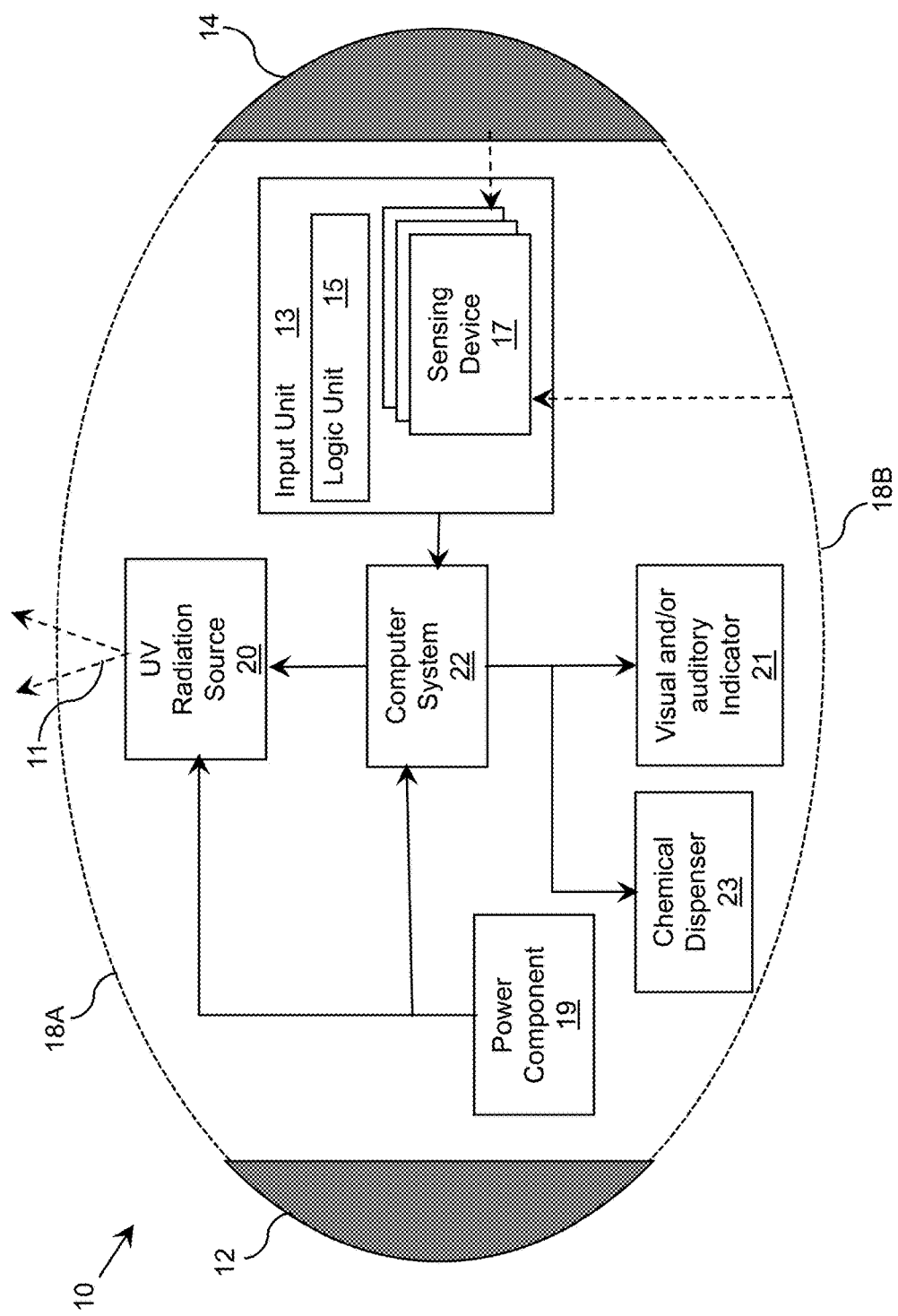
FIG. 3 shows an illustrative system according to an embodiment.

Turning now to FIG. 3, an illustrative system located within the enclosure 10 according to an embodiment is shown. The computer system 22 (e.g., the control unit) can be configured to control the set of ultraviolet radiation sources 20 to direct ultraviolet radiation 11 through an ultraviolet transparent window 18A, 18B. Only one ultraviolet radiation source 20 is shown for illustrative purposes and it is understood that any number of ultraviolet radiation sources 20 may be located within the enclosure 10. Furthermore, the ultraviolet transparent window 18A, 18B is shown to extend along the entire side of the enclosure 10. However, it is understood that the ultraviolet transparent window 18A, 18B can occupy only a portion of the side of the enclosure 10. In another embodiment, the ultraviolet transparent material of the windows 18A, 18B can span the entire exterior surface of the enclosure 10. Furthermore, in an embodiment, the enclosure 10 can be covered by a photo-catalyst, such as a layer of titanium dioxide ($TiO_2$), which can assist in sterilization and disinfection.

As discussed herein, physical pressure can be applied to the first end 12 and/or the second end 14 of the enclosure 10 and converted into an electrical signal by sensing devices located at each end 12, 14. The electrical signal(s) can be provided to the computer system 22 for use in controlling the ultraviolet radiation source 20. To this extent, the enclosure 10 can include an input unit 13 for converting the physical pressure into an electrical signal for the computer system 22.

The input unit 13 also can include one or more additional devices. For example, the input unit 13 is shown including a logic unit 15. In an embodiment, the logic unit 15 receives data from a set of sensing devices 17 (e.g., pressure sensors located at each end 12, 14) and provides data for processing by the computer system 22. In an embodiment, the sensing device 17 comprises a piezoelectric crystal or a mechanical switch activated by pressure. In another embodiment, the sensing device 17 can comprise a capacitive sensor, such as capacitive sensors used to provide for user input. In a more particular embodiment, the logic unit 15 can provide information corresponding to the physical pressure applied to one or both the ends 12, 14, e.g., a duration of the pressure, an amount of the pressure, a timing of the pressure, and/or the like. The logic unit 15 can adjust the operation of one or more of the sensing devices 17, operate a unique subset of the sensing devices 17, and/or the like. In response to data received from the input unit 13, the computer system 22 can automatically adjust and control one or more aspects of the ultraviolet radiation 11 generated by the ultraviolet radiation source 20 according to the data received from the input unit 13. The enclosure 10 can also include a visual and/or auditory indicator 21 for indicating an operating status of one or more of the components located therein. For example, the computer system 22 can manage the visual and/or audible indicator 21 to: indicate the on/off state of the components located in the enclosure 10; generate visible light only concurrently with the ultraviolet radiation 11; generate an audible sound at the start and/or completion of generating the ultraviolet radiation 11; indicate a low battery; indicate a malfunctioning ultraviolet radiation source 20; and/or the like.

The input unit 13 can include various types of sensing devices 17. In an embodiment, one or more of the sensing devices 17 can include an ultraviolet radiation detector configured to sense the intensity of the ultraviolet radiation 11 passing through (out of the enclosure and/or into the enclosure) at least one of the ultraviolet transparent windows 18A, 18B. In response to the data received by the sensing device 17 and provided for processing by the computer system 22, the computer system 22 can control and adjust one or more aspects of the ultraviolet radiation 11 generated by the ultraviolet radiation source 20 (e.g., increase or decrease the ultraviolet radiation 11 based on the ultraviolet radiation being reflected back into the enclosure 10).

In another embodiment, one or more of the sensors 17 can comprise an ultraviolet fluorescence sensor, an ultraviolet absorbance sensor, and/or the like. These sensors 17 can acquire data corresponding to a scattering of the UV radiation 11 within an area in which the enclosure 10 is placed. The computer system 22 can process the data corresponding to the scattering of UV radiation to correlate it with, for example, a level of contamination in a fluid located in the area and/or the items located within the area, and make any adjustments to the operation of the ultraviolet sources 20 accordingly. Similarly, the computer system 22 can process data acquired by the sensor 17 to maintain a target level of ultraviolet flux.

For each embodiment of the enclosure 10 including the ultraviolet radiation source(s) 20, the enclosure 10 can be configured to provide at least a target amount of mechanical protection enclosure 10. For example, the target amount of mechanical protection can provide at least ten feet drop protection, which can be measured by a drop test. The drop test can include dropping the enclosure 10 from a height of approximately ten feet. This drop test can be performed multiple times, while capturing images of the landing each time. The enclosure 10 can be examined after each drop to ensure the no significant damage has occurred. Furthermore, the various components located within the enclosure 10 can be operated and evaluated for continued proper operation after one or more of the drops. In an embodiment, portions of an exterior of the enclosure 10 can include a material that absorbs the impact from the drop. For instance, portions of the exterior of the enclosure 10 can be made of rubber or plastic. Additionally, the material can rubberized polycarbonate, polycarbonate, an acrylonitrile butadiene styrene (ABS) composite, polyurethane composites, and/or the like.

The enclosure 10 can include a chemical dispenser 23 for releasing an antibacterial chemical. In applications not related to the preservation and disinfection of food items, the chemical dispenser 23 can release a chemical including alcohol, and/or the like, which can be used for further disinfection purposes.

Figure 4:
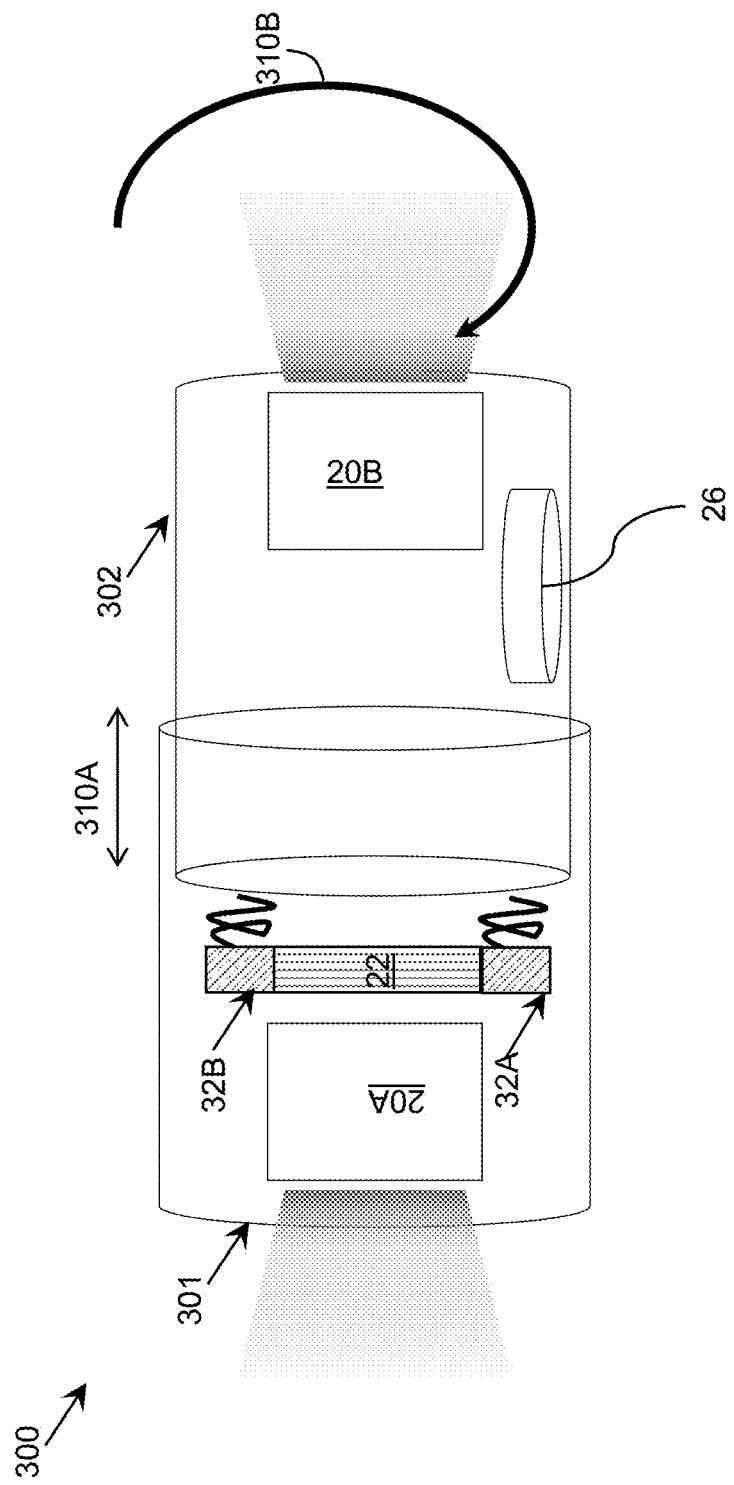
FIG. 4 shows an illustrative enclosure according to an embodiment.

Turning now to FIG. 4, an illustrative enclosure 300 according to an embodiment is shown. In this embodiment, the enclosure 300 can include a first ultraviolet radiation source 20A and a second ultraviolet radiation source 20B radiating in opposing directions. Although two ultraviolet radiation sources are shown, it is understood that the enclosure 300 can include any number of one or more ultraviolet radiation sources. The enclosure 300 can include a first cylinder 301 and a second cylinder 302. The second cylinder 302 can be capable of a transverse motion 310A into the interior of the first cylinder 301 or a rotational motion 310B. The transverse motion 310A and/or the rotational motion 310B can activate a power source 26 within the enclosure 300 and/or generate current that powers the first and second ultraviolet radiation sources 20A, 20B. Similar to the embodiment shown in FIG. 1, the enclosure 300 can include a vibrational power generator with electro-mechanical means (e.g., magnets suspended by springs) or piezo-electric crystals that convert an applied pressure into an electrical signal.

Figure 5:
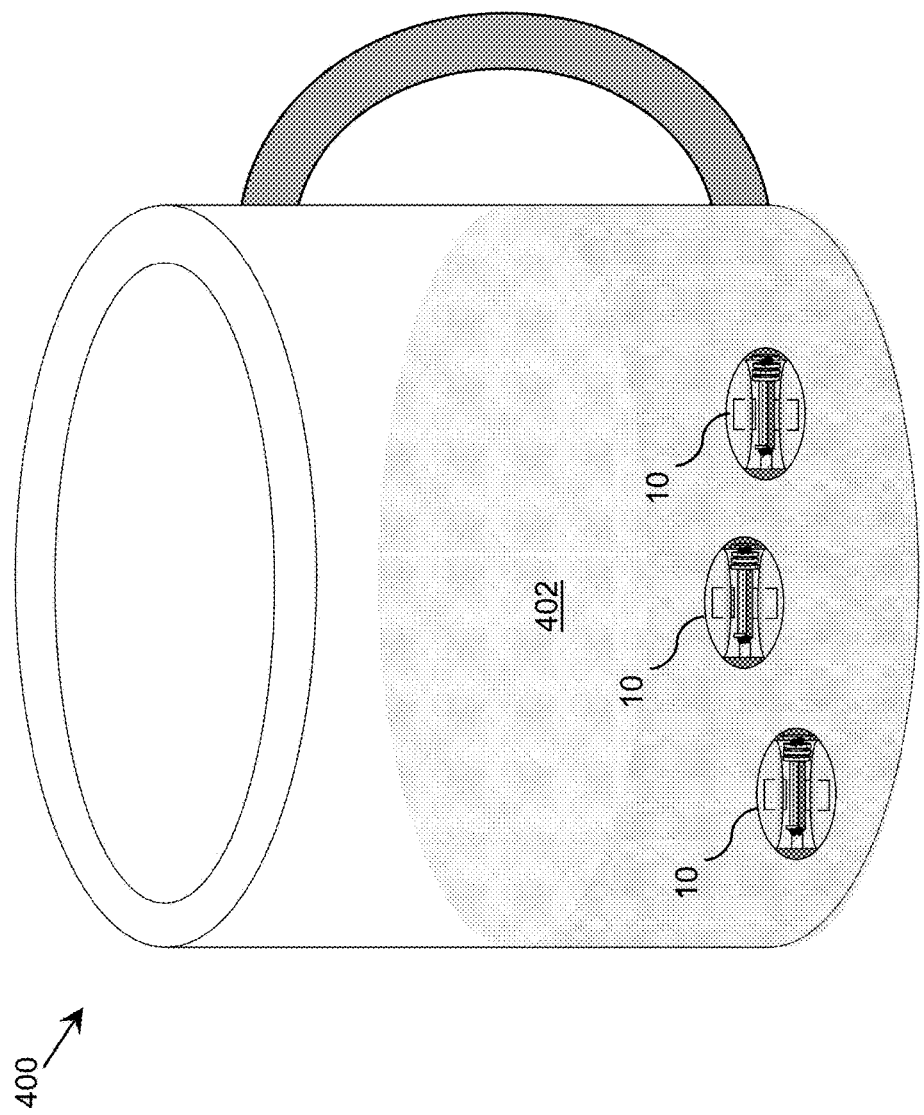
FIG. 5 shows a cup including several illustrative enclosures according to an embodiment.

Turning now to FIG. 5, a container (e.g., a cup) 400 including several illustrative enclosures 10 (FIG. 1) according to an embodiment is shown. The cup 400 can include a liquid 402 for the enclosures 10 to disinfect. Prior to submerging the enclosures 10 into the liquid 402 for disinfection, the components of the enclosures 10 can be turned on, e.g., by applying pressure to the ends 12, 14 to turn on the set of ultraviolet radiation sources 20A, 20B within each enclosure 10. The enclosure 10 can include a neutral buoyancy for the corresponding fluid 402 so that the enclosure 10 is properly submerged in the fluid 402. It is understood that the cup 400 is only an illustrative example of an area in which one or more of the enclosures 10 can be used to disinfect and that other areas can be used. For example, the enclosures 10 can be used to disinfect washers, dryers, dishwashers, refrigerators, food containers, bags, and/or the like.

Figure 6:
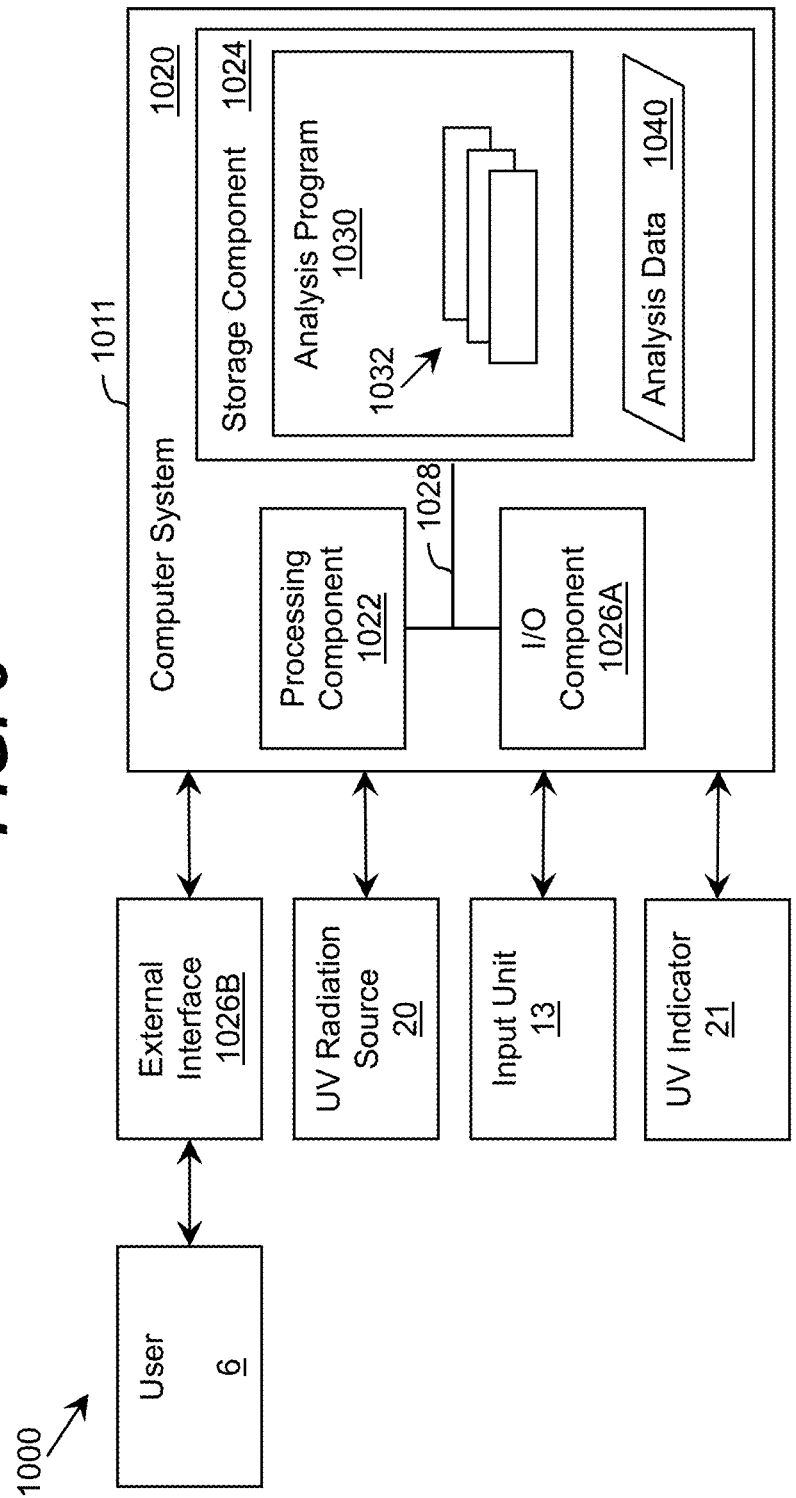
FIG. 6 shows an illustrative environment according to an embodiment.

FIG. 6 shows an illustrative system 1000 according to an embodiment. In this case, the system 1000 includes a monitoring and/or control system 1011, which is implemented as a computer system 1020 including an analysis program 1030, which makes the computer system 1020 operable to manage an ultraviolet (UV) radiation source 20 by performing a process described herein. Portions of the system 1000 can be located within the enclosure 10 (FIG. 1), as discussed herein. In particular, the analysis program 1030 can enable the computer system 1020 to operate the UV radiation source 20 to generate and direct ultraviolet radiation through an ultraviolet transparent window of the enclosure 10 and process data corresponding to one or more conditions of the area and/or an item located in the area, which is acquired by an input unit 13. While a single UV radiation source 20 is shown, it is understood that the enclosure can include any number of one or more UV radiation sources 20, the operation of which the computer system 1020 can separately manage using a process described herein.

The computer system 1020 is shown including a processing component 1022 (e.g., one or more processors), a storage component 1024 (e.g., a storage hierarchy), an input/output (I/O) component 1026 (e.g., one or more I/O interfaces and/or devices), and a communications pathway 1028. In general, the processing component 1022 executes program code, such as the analysis program 1030, which is at least partially fixed in storage component 1024. While executing program code, the processing component 1022 can process data, which can result in reading and/or writing transformed data from/to the storage component 1024 and/or the I/O component 1026 for further processing. The pathway 1028 provides a communications link between each of the components in the computer system 1020. The I/O component 1026 can comprise one or more human I/O devices, which enable a human user 1012 to interact with the computer system 1020 and/or one or more communications devices to enable a system user 1012 to communicate with the computer system 1020 using any type of communications link. To this extent, the analysis program 1030 can manage a set of interfaces (e.g., graphical user interface(s), application program interface, and/or the like) that enable human and/or system users 1012 to interact with the analysis program 1030. Furthermore, the analysis program 1030 can manage (e.g., store, retrieve, create, manipulate, organize, present, etc.) the data, such as analysis data 1040, using any solution.

In any event, the computer system 1020 can comprise one or more general purpose computing articles of manufacture (e.g., computing devices) capable of executing program code, such as the analysis program 1030, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the analysis program 1030 can be embodied as any combination of system software and/or application software.

Furthermore, the analysis program 1030 can be implemented using a set of modules 1032. In this case, a module 1032 can enable the computer system 1020 to perform a set of tasks used by the analysis program 1030, and can be separately developed and/or implemented apart from other portions of the analysis program 1030. As used herein, the term "component" means any configuration of hardware, with or without software, which implements the functionality described in conjunction therewith using any solution, while the term "module" means program code that enables a computer system 1020 to implement the actions described in conjunction therewith using any solution. When fixed in a storage component 1024 of a computer system 1020 that includes a processing component 1022, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 1020.

When the computer system 1020 comprises multiple computing devices, each computing device can have only a portion of the analysis program 1030 fixed thereon (e.g., one or more modules 1032). However, it is understood that the computer system 1020 and the analysis program 1030 are only representative of various possible equivalent computer systems that may perform a process described herein. To this extent, in other embodiments, the functionality provided by the computer system 1020 and the analysis program 1030 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 1020 includes multiple computing devices, the computing devices can communicate over any type of communications link. Furthermore, while performing a process described herein, the computer system 1020 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols. Furthermore, the computer system 1020 can be programmed via WiFi. In this embodiment, the computer system 1020 can provide reports to the user 6 or one or more other computer systems via WiFi regarding any aspect to the illustrative environment 1000, including, but not limited to the bacterial contamination outside of the enclosure 10 (FIG. 1), the current operating aspects of the ultraviolet radiation source 20, the history of the operation of the ultraviolet radiation source 20, the inputs provided to the enclosure 10, and/or the like.

While shown and described herein as a method and system for disinfecting an area using ultraviolet radiation, it is understood that aspects of the invention further provide various alternative embodiments. For example, in one embodiment, the invention provides a computer program fixed in at least one computer-readable medium, which when executed, enables a computer system to disinfect an area using ultraviolet radiation. To this extent, the computer-readable medium includes program code, such as the analysis program 1030 (FIG. 6), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 1030 (FIG. 6), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for disinfecting an area using ultraviolet radiation. In this case, the generating can include configuring a computer system, such as the computer system 1020 (FIG. 6), to implement the method of disinfecting an area using ultraviolet radiation. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
an enclosure including at least one ultraviolet transparent window forming an exterior surface of the enclosure, the enclosure including a first end and a second end that provide a waterproof seal for an interior of the enclosure;
a power component located within the enclosure;
a set of ultraviolet radiation sources located adjacent to the at least one ultraviolet transparent window, the set of ultraviolet radiation sources configured to generate ultraviolet radiation directed through the at least one ultraviolet transparent window and out of the enclosure;
an input unit located on at least one end of the enclosure and configured to generate a set of electrical signals corresponding to a pattern of pressure applied to the at least one end of the enclosure, wherein the input unit is distinct from the at least one ultraviolet transparent window, and wherein the pattern of pressure is a series of two or more applied pressures of a minimum amount with a pause between each applied pressures, wherein the applied pressures and the pauses have a corresponding target time duration; and
a control unit configured to manage the ultraviolet radiation by performing a method comprising:
monitoring the set of electrical signals generated by the input unit; and
controlling, based on the monitoring, the ultraviolet radiation generated by the set of ultraviolet radiation sources, wherein the pattern of pressure applied to the at least one end of the enclosure indicates a set of parameters for the ultraviolet radiation, wherein the set of parameters includes at least one of: a direction, a wavelength, an intensity, or a pattern, of the ultraviolet radiation generated by the set of ultraviolet radiation sources.

2. The system of claim 1, further comprising a logic unit configured to convert mechanical energy of the pattern of pressure applied to the input unit into the set of electrical signals.

3. The system of claim 1, wherein the at least one ultraviolet transparent window comprises an ultraviolet transparent polymer.

4. The system of claim 1, wherein the input unit further comprises at least one capacitive sensor configured to convert a capacitive touch applied to the capacitive sensor into an electrical signal.

5. The system of claim 1, further comprising a set of ultraviolet detectors configured to detect an amount of ultraviolet radiation and provide data corresponding to the amount of ultraviolet radiation to the control unit.

6. The system of claim 5, wherein the control unit further monitors the amount of detected ultraviolet radiation and adjusts, in response to the monitoring of the detected ultraviolet radiation, the ultraviolet radiation generated by the set of ultraviolet radiation sources.

7. The system of claim 1, further comprising a chemical dispenser located within the enclosure, wherein the chemical dispenser is configured to release an antibacterial chemical out of the enclosure.

8. An enclosure, comprising:
a first end and a second end that provide a waterproof seal for an interior of the enclosure;
at least one ultraviolet transparent region forming an exterior surface of the enclosure;
a set of ultraviolet radiation sources located within the enclosure, the set of ultraviolet radiation sources configured to generate ultraviolet radiation directed through the at least one ultraviolet transparent region and out of the enclosure;
a power component located within the enclosure;
an input unit located on at least one end of the enclosure and configured to generate a set of electrical signals corresponding to a pattern of pressure applied to the at least one end of the enclosure, wherein the input unit is distinct from the at least one ultraviolet transparent region, and wherein the pattern of pressure is a series of two or more applied pressures of a minimum amount with a pause between each applied pressures, wherein the applied pressures and the pauses have a corresponding target time duration; and
a control unit configured to manage the ultraviolet radiation by performing a method comprising:
monitoring the set of electrical signals generated by the input unit; and
controlling, based on the monitoring, the ultraviolet radiation generated by the set of ultraviolet radiation sources, wherein the pattern of pressure applied to the at least one end of the enclosure indicates a set of parameters for the ultraviolet radiation, wherein the set of parameters includes at least one of: a direction, a wavelength, an intensity, or a pattern, of the ultraviolet radiation generated by the set of ultraviolet radiation sources.

9. The enclosure of claim 8, wherein the enclosure has a prolate spheroid shape.

10. The enclosure of claim 9, wherein the input unit is configured to generaten the set of electrical signals in response to the pattern of pressure applied substantially concurrently to both the first end and the second end of the prolate spheroid shape.

11. The enclosure of claim 8, wherein the at least one ultraviolet transparent region forms substantially all of a side extending between the first end and the second end of the enclosure.

12. The enclosure of claim 8, wherein the exterior surface of the enclosure is covered by $TiO_2$.

13. The enclosure of claim 8, further comprising a set of ultraviolet detectors located within the enclosure and configured to detect an amount of ultraviolet radiation entering the enclosure through the at least one ultraviolet transparent region, and provide data corresponding to the amount of ultraviolet radiation to the control unit.

14. The enclosure of claim 13, wherein the control unit monitors the amount of detected ultraviolet radiation and adjusts, in response to the monitoring of the detected ultraviolet radiation, the ultraviolet radiation generated by the set of ultraviolet radiation sources.

15. The enclosure of claim 8, further comprising a chemical dispenser located within the enclosure, wherein the chemical dispenser is configured to release an antibacterial chemical out of the enclosure.

16. A system comprising:
an area including a fluid for disinfection; and
at least one enclosure submerged within the fluid, the at least one enclosure comprising:
a first end and a second end that provide a waterproof seal for an interior of the at least one enclosure;
at least one ultraviolet transparent window forming an exterior surface of the at least one enclosure;
a set of ultraviolet radiation sources located within the at least one enclosure, the set of ultraviolet radiation sources configured to generate ultraviolet radiation directed through the at least one ultraviolet transparent window and out of the at least one enclosure into the fluid;
a power component located within the at least one enclosure;
an input unit located on at least one end of the at least one enclosure and configured to generate a set of electrical signals corresponding to a pattern of pressure applied to the at least one end of the at least one enclosure, wherein the input unit is distinct from the at least one ultraviolet transparent window, and wherein the pattern of pressure is a series of two or more applied pressures of a minimum amount with a pause between each applied pressures, wherein the applied pressures and the pauses have a corresponding target time duration; and
a control unit configured to manage the ultraviolet radiation by performing a method comprising:
monitoring the set of electrical signals generated by the input unit; and
controlling, based on the monitoring, the ultraviolet radiation generated by the set of ultraviolet radiation sources, wherein the pattern of pressure applied to the at least one end of the at least one enclosure indicates a set of parameters for the ultraviolet radiation, wherein the set of parameters includes at least one of: a direction, a wavelength, an intensity, or a pattern, of the ultraviolet radiation generated by the set of ultraviolet radiation sources.

17. The system of claim 16, wherein the input unit is configured to generate the set of electrical signals in response to pressure applied substantially simultaneously to the first end and the second end of the at least one enclosure.

18. The system of claim 16, wherein the at least one enclosure further comprises a set of ultraviolet detectors configured to detect an amount of ultraviolet radiation reflected by the fluid.

19. The system of claim 18, wherein the control unit monitors the amount of detected ultraviolet radiation and adjusts, in response to the monitoring of the detected ultraviolet radiation, the ultraviolet radiation generated by the set of ultraviolet radiation sources.

20. The system of claim 16, wherein the at least one enclosure further comprises a chemical dispenser located within the at least one enclosure, wherein the chemical dispenser is configured to release an antibacterial chemical out of the enclosure.

* * * * *

UNITED STATES PATENT AND TRADEMARK OFFICE
CERTIFICATE OF CORRECTION

PATENT NO. : 9,833,526 B2
APPLICATION NO. : 14/630692
DATED : December 5, 2017
INVENTOR(S) : Igor Agafonov et al.

It is certified that error appears in the above-identified patent and that said Letters Patent is hereby corrected as shown below:

In the Claims

Column 12, Line 67 (Claim 10, Line 2), "configured to generaten the set" should read – configured to generate the set –.

Signed and Sealed this
Twenty-fourth Day of April, 2018

Andrei Iancu
*Director of the United States Patent and Trademark Office*